United States Patent

Yu et al.

(10) Patent No.: US 9,795,505 B2
(45) Date of Patent: Oct. 24, 2017

(54) ARTICULATING OPHTHALMIC SURGICAL PROBE

(75) Inventors: Xiaoyu Yu, San Diego, CA (US); Christopher McCollam, Irvine, CA (US); Jack Auld, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 4 days.

(21) Appl. No.: 13/563,992

(22) Filed: Aug. 1, 2012

(65) Prior Publication Data

US 2013/0035551 A1 Feb. 7, 2013

Related U.S. Application Data

(60) Provisional application No. 61/514,751, filed on Aug. 3, 2011.

(51) Int. Cl.
*A61B 1/00* (2006.01)
*A61F 9/007* (2006.01)
(Continued)

(52) U.S. Cl.
CPC ........ *A61F 9/00736* (2013.01); *A61B 1/0052* (2013.01); *A61B 1/0055* (2013.01);
(Continued)

(58) Field of Classification Search
CPC .......... A61M 25/0133; A61M 25/0136; A61M 25/0138; A61M 25/0147; A61B 1/0052;
(Continued)

(56) References Cited

U.S. PATENT DOCUMENTS 4,911,148 A * 3/1990 Sosnowski et al. .......... 600/146
4,941,455 A * 7/1990 Watanabe ............ A61B 1/0052
600/146
(Continued)

FOREIGN PATENT DOCUMENTS

JP 62007848 B 2/1987
JP 09024019 A 1/1997
(Continued)

OTHER PUBLICATIONS

H. Fischer et al., Flexible distal tip made of nitinol (NiTi) for a steerable endoscopic camera system, 780-783, (1999), Materials Science and Engineering A273-275.†

*Primary Examiner* — Timothy J Neal
*Assistant Examiner* — Aaron B Fairchild

(57) ABSTRACT

An articulating optical surgical probe includes a handle sized to fit in a single hand and a single rigid cannula extending from the handle having a diameter of 20 Ga or less. The probe further includes a slotted tip at a distal end of the cannula and at least one optical fiber extending through the handle, the single rigid cannula and the slotted tip, and a pull-wire secured to the slotted tip. When the pull-wire exerts tension on the slotted tip, the slotted tip will deviate from straight to a bend angle controlled by the tension in the pull-wire. The slotted tip is formed from a resilient material that will restore to the straight position when the tension exerted by the pull-wire is released.

24 Claims, 6 Drawing Sheets

(51) Int. Cl.
*A61B 1/005* (2006.01)
*A61B 17/00* (2006.01)

(52) U.S. Cl.
CPC ........ *A61B 1/0057* (2013.01); *A61B 1/00073* (2013.01); *A61B 1/00165* (2013.01); *A61B 2017/00309* (2013.01)

(58) Field of Classification Search
CPC A61B 2017/00309; A61B 2017/00323; A61B 2017/00327; A61B 1/0051; A61B 1/0016; A61B 2017/003; A61B 1/0057; A61B 34/71; B25J 9/1045; Y10T 74/20323
USPC ...... 600/139–141, 146–150, 138; 604/95.01, 604/95.04, 280, 523, 528
See application file for complete search history.

(56) References Cited

U.S. PATENT DOCUMENTS

| | | | |
|---|---|---|---|
| 4,986,257 A | | 1/1991 | Chikama |
| 5,195,968 A | * | 3/1993 | Lundquist et al. ........ 604/95.04 |
| 5,275,151 A | * | 1/1994 | Shockey et al. ............. 600/146 |
| 5,275,593 A | | 1/1994 | Easley et al. |
| 5,284,128 A | * | 2/1994 | Hart ............................ 600/208 |
| 5,381,782 A | | 1/1995 | DeLaRama et al. |
| 5,448,989 A | | 9/1995 | Heckele |
| 5,452,836 A | | 9/1995 | Huitema et al. |
| 5,549,542 A | * | 8/1996 | Kovalcheck ........ A61B 1/0052 600/146 |
| 5,810,716 A | * | 9/1998 | Mukherjee et al. ......... 600/146 |
| 6,019,780 A | | 2/2000 | Lombardo et al. |
| 6,572,608 B1 | | 6/2003 | Lee et al. |
| 7,402,158 B2 | | 7/2008 | Scheller et al. |
| 7,473,249 B2 | | 1/2009 | Scheller et al. |
| 7,637,905 B2 | | 12/2009 | Saadat et al. |
| 7,783,346 B2 | | 8/2010 | Smith et al. |
| 2002/0052155 A1 | | 5/2002 | Campbell et al. |
| 2002/0072720 A1 | | 6/2002 | Hague et al. |
| 2002/0176132 A1 | | 11/2002 | Sarraf |
| 2003/0069522 A1 | * | 4/2003 | Jacobsen et al. ............. 600/585 |
| 2004/0181138 A1 | † | 9/2004 | Hindricks |
| 2005/0096590 A1 | * | 5/2005 | Gullickson et al. ........ 604/95.04 |
| 2006/0135961 A1 | * | 6/2006 | Rosenman et al. ........ 604/95.04 |
| 2006/0184162 A1 | | 8/2006 | Smith |
| 2008/0058761 A1 | | 3/2008 | Spaide |
| 2008/0125628 A1 | | 5/2008 | Ueno et al. |
| 2008/0188910 A1 | | 8/2008 | Spaide |
| 2008/0287938 A1 | | 11/2008 | Scheller et al. |
| 2009/0292199 A1 | | 11/2009 | Bielewicz et al. |
| 2010/0160730 A1 | | 6/2010 | Konomura |
| 2011/0166422 A1 | | 7/2011 | Ross et al. |

FOREIGN PATENT DOCUMENTS

| | | |
|---|---|---|
| JP | 03060623 A | 2/2003 |
| JP | 2007000427 A | 1/2007 |
| JP | 5160549 B2 | 2/2013 |
| RU | 2416383 C2 | 4/2011 |

\* cited by examiner
† cited by third party

ARTICULATING OPHTHALMIC SURGICAL PROBE

RELATED APPLICATIONS

This application claims priority to U.S. provisional application Ser. No. 61/514,751, filed on Aug. 3, 2011, the contents which are incorporated herein by reference.

FIELD OF THE INVENTION

This invention relates to ophthalmic surgical equipment and more particularly to posterior segment ophthalmic surgical probes.

BACKGROUND OF THE INVENTION

Microsurgical instruments typically are used by surgeons for removal of tissue from delicate and restricted spaces in the human body, particularly in surgery on the eye, and more particularly in procedures for removal of the vitreous body, blood, scar tissue, or the crystalline lens. Such instruments include a control console and a surgical handpiece with which the surgeon dissects and removes the tissue. With respect to posterior segment surgery, the handpiece may be a vitreous cutter probe, a laser probe, or an ultrasonic fragmenter for cutting or fragmenting the tissue and is connected to the control console by a long air-pressure (pneumatic) line and/or power cable, optical cable, or flexible tubes for supplying an infusion fluid to the surgical site and for withdrawing or aspirating fluid and cut/fragmented tissue from the site. The cutting, infusion, and aspiration functions of the handpiece are controlled by the remote control console that not only provides power for the surgical handpiece(s) (e.g., a reciprocating or rotating cutting blade or an ultrasonically vibrated needle), but also controls the flow of infusion fluid and provides a source of vacuum (relative to atmosphere) for the aspiration of fluid and cut/fragmented tissue. The functions of the console are controlled manually by the surgeon, usually by means of a foot-operated switch or proportional control.

During posterior segment surgery, the surgeon typically uses several handpieces or instruments during the procedure. This procedure requires that these instruments be inserted into, and removed out of the incision. This repeated removal and insertion can cause trauma to the eye at the incision site. To address this concern, hubbed cannulae were developed at least by the mid-1980s. These devices consist of a narrow tube with an attached hub. The tube is inserted into an incision in the eye up to the hub, which acts as a stop, preventing the tube from entering the eye completely. Surgical instruments can be inserted into the eye through the tube, and the tube protects the incision sidewall from repeated contact by the instruments. In addition, the surgeon can use the instrument, by manipulating the instrument when the instrument is inserted into the eye through the tube, to help position the eye during surgery.

Many surgical procedures require access to the sides or forward portion of the retina. In order to reach these areas, the surgical probes must be pre-bent or must be bendable intra-operatively. Various articulating optical surgical probes for providing laser and/or illumination light are known. See for example, U.S. Pat. No. 5,281,214 (Wilkins, et al.) and U.S. Pat. No. 6,984,130 (Scheller, et al.). The articulation mechanism, however, adds extra complexity and expense. One flexible laser probe needing no articulation mechanism is commercially available, but this device uses a relatively large diameter optical fiber sheathed in a flexible tube comprising the distal tip, resulting in a large bend radius and large distal tip diameter with significant bend stiffness. These characteristics require that the distal tip contain a non-bent straight portion for ease of insertion of the bent portion, which must flexibly straighten as it passes through the hubbed cannula. The straight portion of the distal tip allows the bent portion to flexibly pass through the hubbed cannula before the distal cannula of the handpiece enters the hubbed cannula, to allow maximum bending clearance of the flexible portion, thereby minimizing the bending strain and corresponding frictional insertion forces. Such a large bend radius, large diameter flexible tube, and straight distal tip causes the useable portion of the fiber to extend a relatively long distance from the distal tip of the probe and limits access of the probe.

A further disadvantage in the known art is the flexibility of the distal cannula, which is a function of the material properties and cross sectional moment of inertia, as determined by the gauge size of the outside diameter of the cannula to fit within the hubbed cannula, and the inside diameter of the cannula to accept the flexible tube. For any given material, the outer and inner diameters of the cannula determine the flexibility of the cannula. This flexibility limits the surgeon's ability to use the instrument to manipulate the position of the eye during surgery.

A flexible-tip probe is disclosed in U.S. Patent Application Publication 2009/0093800 (Auld, et al.) that does not require a straight portion of flexible tube, which thus provides a more compact useable tip length, thereby allowing greater access to internal posterior structures of the eye without compromising insertion forces. The flexible-tip probe provides increased rigidity of the distal cannula to facilitate manipulation of the position in the eye during surgery. While this probe provides a relatively smaller cross section as compared to the previous probes, such as those disclosed by Scheller et al., it does not provide controllable articulation over a range of angles in the manner those probes do.

BRIEF SUMMARY OF THE INVENTION

An articulating optical surgical probe includes a handle sized to fit in a single hand and a single rigid cannula extending from the handle having a diameter of 20 Ga or less. The probe further includes a slotted tip at a distal end of the cannula and at least one optical fiber extending through the handle, the single rigid cannula and the slotted tip, and a pull-wire secured to the slotted tip. When the pull-wire exerts tension on the slotted tip, the slotted tip will deviate from straight to a bend angle controlled by the tension in the pull-wire. The slotted tip is formed from a resilient material that will restore to the straight position when the tension exerted by the pull-wire is released.

Other objectives, features and advantages of the present invention will become apparent with reference to the drawings, and the following description of the drawings and claims.

DETAILED DESCRIPTION OF THE INVENTION

Various embodiments of the present invention may avoid difficulties associated with previous articulating optical surgical probes. In particular, certain embodiments of the present invention may provide a single rigid cannula with a small diameter not only capable of insertion into very small incisions but also capable of articulating in a controlled fashion through a range of angles. Thus, such embodiments of the present invention combine the advantages of a relatively rigid articulating optical surgical probe with the controllable articulation of dual cannula probes that require a larger diameter.

Particular embodiments of the present invention include a single rigid cannula with a slotted tip of resilient material secured to a pull wire. Tension in the pull wire causes the slotted tip to bend in a particular direction, while releasing the tension allows the resilient tip to restore to its straight position. Pull-wire technology has been used previously to deviate a distal end of a surgical catheter, but not in a small-diameter, rigid cannula used in handheld optical surgical probes nor with the degree of angular movement used in the relatively small spaces found within the interior of an eye. Consequently, the application of pull-wire tension in the context of hand-held surgical probes is uniquely advantageous. In particular embodiments of the present invention, one or more of the optical fibers used in the endoprobe 10 may also be used as the pull-wire.

Figure 1:
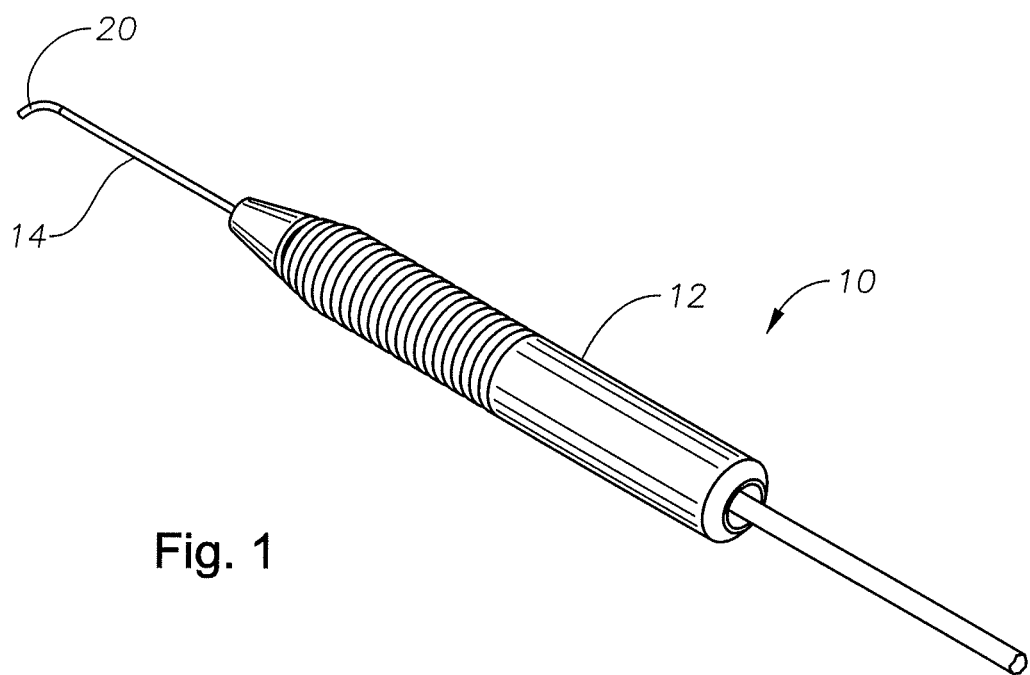
FIG. 1 is a schematic of an articulating optical surgical endoprobe, according to a particular embodiment of the present invention.

FIG. 1 is a schematic of an articulating optical surgical endoprobe 10, according to a particular embodiment of the present invention, with a handle 12 suitable for being held in a single hand and a cannula 14. (For ease of illustration, the handle 12 and cannula 14 are not shown to scale and certain external features of the handle 12, such as the control mechanism for an internal pull-wire, are not shown.) The proximal end of the endoprobe 10 is connected to one or more light sources (not shown) that provide laser and/or illumination light by connection to at least one optical fiber running through the interior of the endoprobe 10.

The cannula 14 is formed of a rigid biocompatible material, such as stainless steel. Endoprobes, according to various embodiments of the present invention, use a "single" rigid cannula, referring to the fact that there is no other relatively rigid, self-supporting cannula formed separately inside or outside the single cannula and/or independently movable with respect to the single cannula. However, the term "single" is not intended to exclude the use of multiple layers or coatings to form the single cannula, nor does it exclude the use of soft polymer sleeves or sheaths that conform to the shape of the cannula. The cannula 14 has a slotted tip 20 at a distal end (referring to the end farthest from the surgeon during use). The slotted tip 20 may articulate in a selected direction in a controllable manner by applying tension to a pull wire secured within the slotted tip 20 (not shown in FIG. 1).

The slotted tip 20 is formed from a resilient material, referring to a material that can restore to the straight orientation after the tension from the pull-wire is removed. The resilient material for the slotted material may be, for example, nitinol, which can be both sufficiently rigid to insert through an incision hub and sufficiently resilient to restore after articulation. Other metals, such as spring steel, or other materials with similar properties known in the art could be used. Depending on the particular slot configuration of the slotted tip, it may be possible to use relatively rigid materials that are not exceptionally elastic, such as stainless steel, Ni-base super-alloys, Co—Cr alloys, or the like without applying so much force as to exceed the yield point and permanently deform the material. The resilient materials may themselves be biocompatible, or they could be enclosed in another material, such as a polymer sheath, to prevent contact with tissue. The cannula 14 and the slotted tip 20 can be, but need not be, formed from the same material. The cannula 14 and/or the slotted tip 20 may also be coated with a stiffening material, such as synthetic diamond or metal plating (e.g., chromium), to provide improved stiffness for insertion into an incision hub and to reduce the likelihood of breakage.

Figure 2:
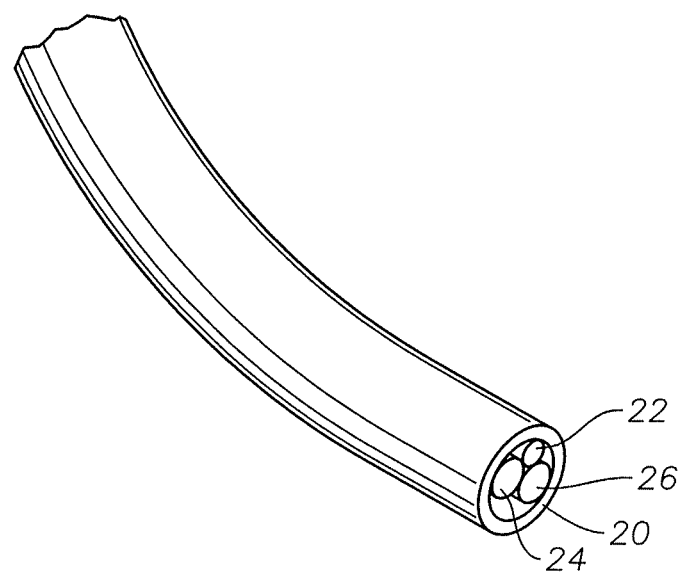
FIG. 2 illustrates an end view of an example of a slotted tip 20 according to a particular embodiment of the present invention.

FIG. 2 illustrates an end view of an example of a slotted tip 20 according to a particular embodiment of the present invention. In the embodiment depicted in FIG. 2, a pull-wire 22 is secured to what is shown as the top side of the slotted tip 20. The slotted tip 20 encloses two optical fibers 24 and 26, an illumination fiber 24 having a diameter of 183 μm and a laser fiber 26 having a diameter of 108 μm. Allowing for the width of the slotted tip 20, this allows for the diameter of the cannula 14 to be made smaller relative to dual cannula systems.

Figure 3A:
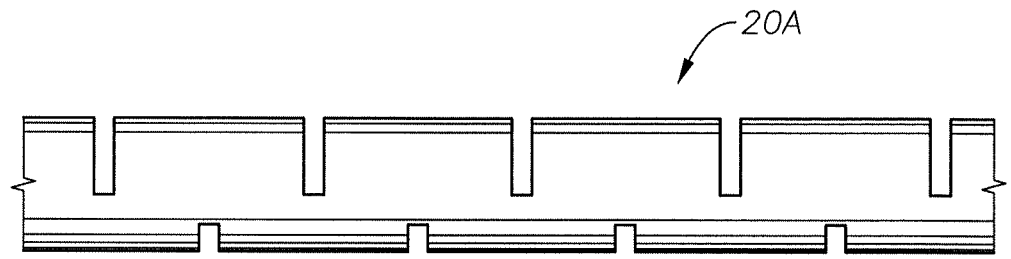
FIGS. 3A-3H illustrate various slot designs for a slotted tip according to particular embodiments of the present invention.
Figure 3B:
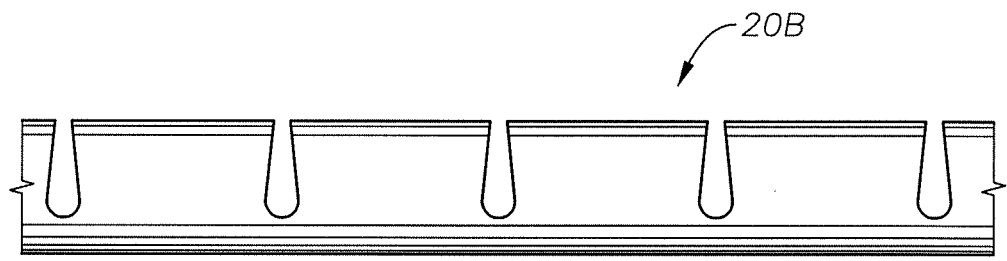
Figure 3C:
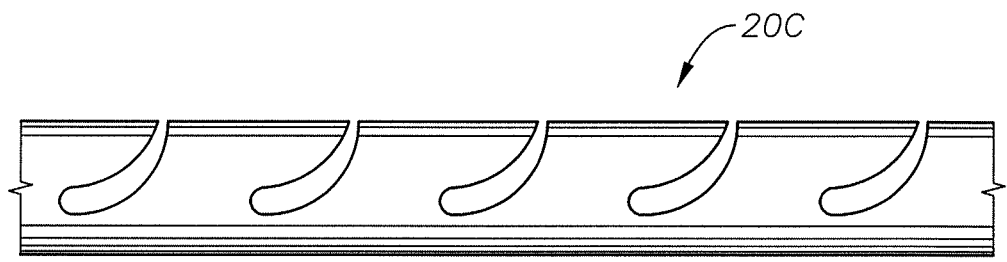

FIGS. 3A-3H illustrate various slot designs for the slotted tip 20 according to particular embodiments of the present invention (respectively labeled as "20A," "20B," etc., and collectively referred to as "slotted tip 20"). In FIG. 3A, slots deeper than the radius of the slotted tip 20A are cut into the side of the slotted tip 20A toward which the slotted tip 20A is to bend. Shallow slots are cut into the opposite side permitting that side to bend as well. FIGS. 3B and 3C illustrate straight and curved "keyhole" slots having a wider base as the slot extends deeper into the respective slotted tips 20B and 20C. The wider base reduces the amount of force required to deviate the slotted tip 20B or 20C to its curved position, potentially making the endoprobe 10 more comfortable to use.

Figure 3D:
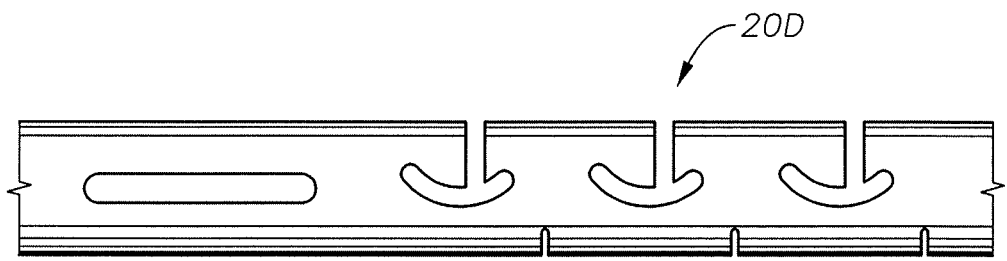
Figure 3E:
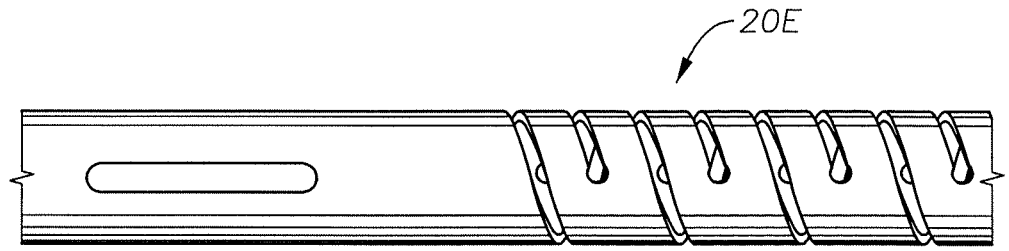
Figure 3F:
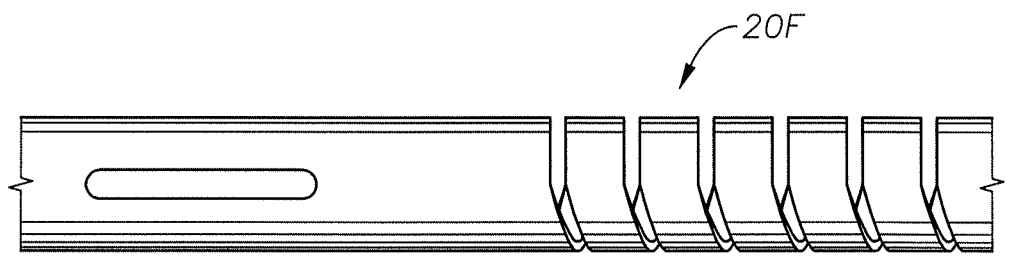
Figure 3G:
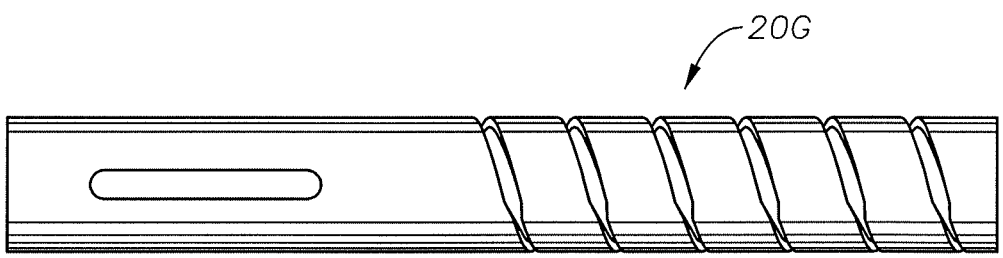

FIGS. 3D-3G illustrate slot designs that can be used for more rigid tip materials to allow the slotted tip 20 to resiliently restore to the straight position after being deviated into the curved position. In FIG. 3D, slots that are generally oblong along the length of the cannula 14 are set opposed to shallow back slots, which tends to reduce the force required to deviate the slotted tip 20D to the curved position. In FIG. 3E, a continuous spiral cut, allowing the slotted tip 20E to bend, is interspersed with back slots (in this case, keyhole slots), causing the slotted tip 20E to bend in the direction of the back slots. FIG. 3F shows a spiral cut pattern wherein the spiral path is perpendicular to the longitudinal axis of the slotted tip 20F on one side, causing the slotted tip 20F to preferentially deviate toward the side where the spiral path is perpendicular. FIG. 3G shows a spiral cut pattern with the cut widened selective on one side, causing slotted tip 20G to selectively deviate toward the side where the spiral cut is wider.

Figure 3H:
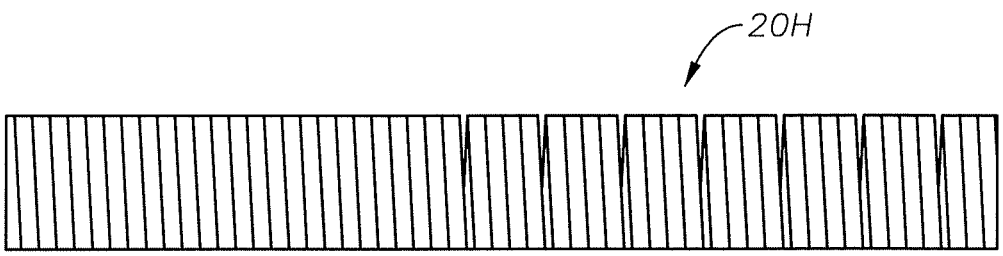

FIG. 3H shows a slotted tip 20H formed out of a wound wire of material, such as by winding material drawn into wires around a mandrel. At a proximal and distal end of the slotted tip 20H the coils of the wound wire are welded together. In the intermediate region between the proximal and distal ends, one side of the tube has widened interstitial slots formed between the coils of the wound wire, causing the slotted tip 20H to selectively deviate toward the widened slots when tension is applied via the pull-wire. Forming the slotted tip 20 of a wound wire of material may have advantages by permitting the use of materials that can more easily be formed into wires than tubes. Although a single wound wire is shown in FIG. 3H, multiple wire strands could also be used.

Figure 4A:
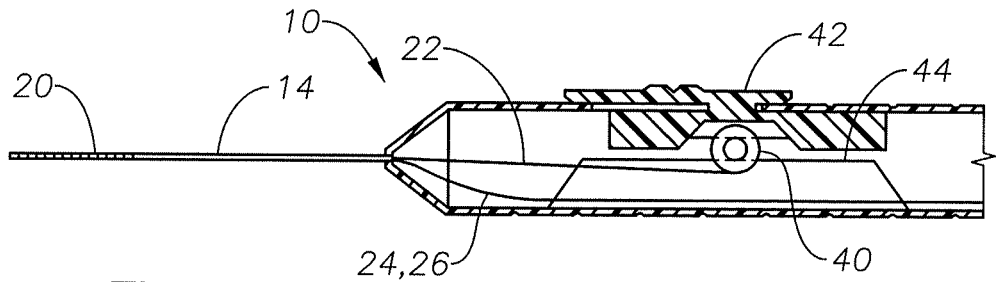
FIGS. 4A-4K illustrate various mechanisms for increasing the tension in the pull-wire 22 according to particular embodiments of the present invention.
Figure 4B:
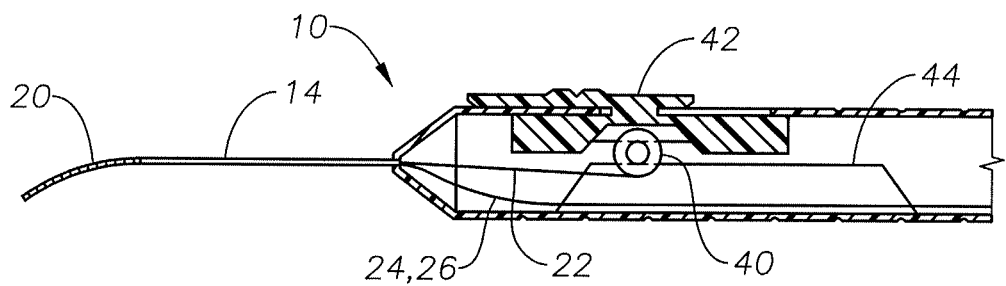

FIGS. 4A-4K illustrate various mechanisms for increasing the tension in the pull-wire 22 according to particular embodiments of the present invention. In FIGS. 4A and 4B, the pull-wire 22 is wound on a pinion 40 secured between a control button 42 and a base 44. The pinion 40 comprises two surfaces, a smaller diameter surface r which rolls between the control button 42 and a base 44, and a larger diameter surface R about which the pull wire 22 winds. The radial difference between the smaller and larger diameter surfaces r and R results in a differential displacement Δ1 in the pull wire as the pinion 40 rotates and translates. By selecting appropriate diameters for the smaller and larger diameter surfaces r and R, a relatively small amount of pull wire displacement Δ1 can be achieved during a relatively large amount of control button translation, providing the user with precise control over the deflection in the slotted tip 20. In one embodiment, the smaller diameter surface r comprises gear teeth with mating gear teeth on the control button 42 and the base 44. This may reduce the likelihood of slippage.

Figure 4C:
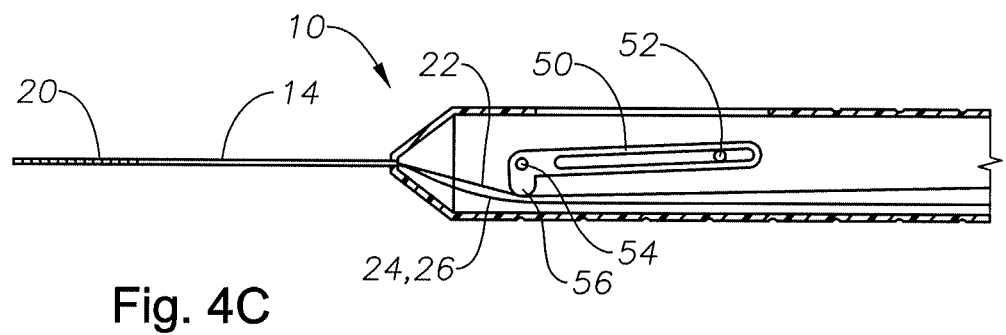
Figure 4D:
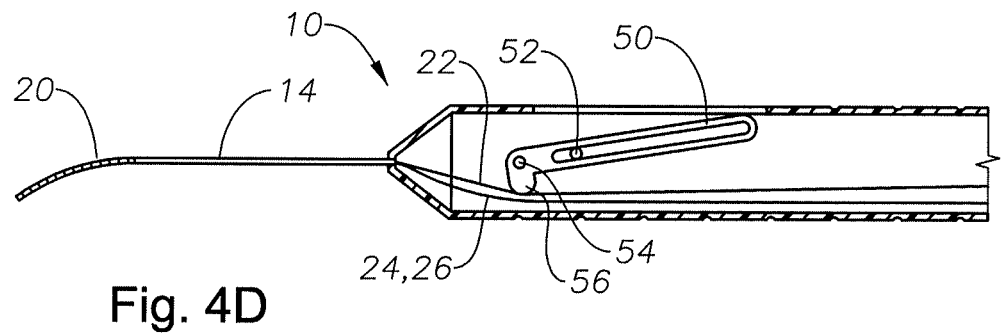
Figure 4E:
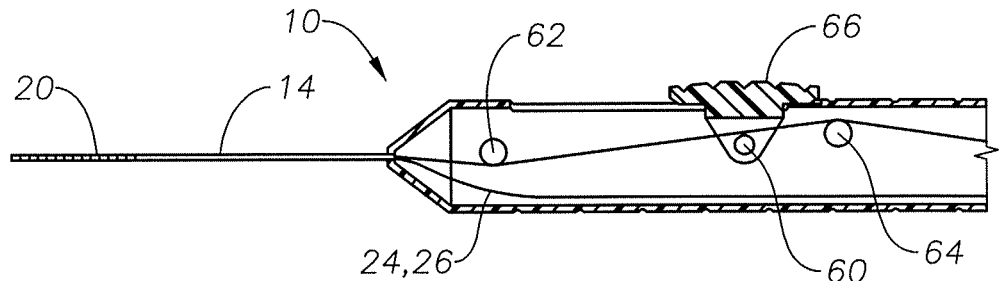
Figure 4F:
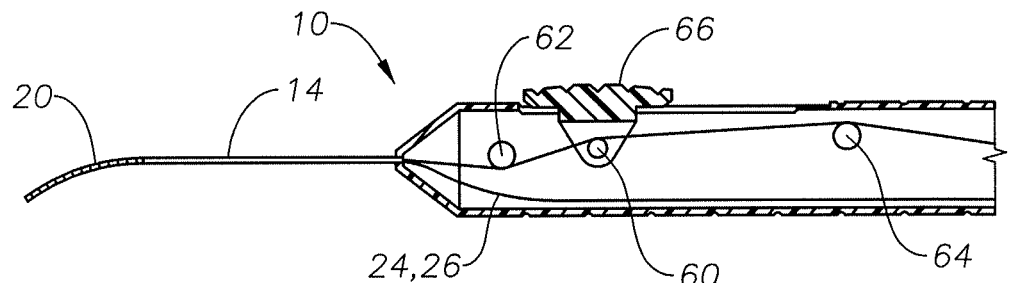

FIGS. 4C and 4D illustrate a lever arm 50 with a sliding actuation pin 52 held in place by a fixed pin 54 at a pivot of the arm. A control button (not shown) can be used to advance the sliding pin 52, permitting the proximal portion of the lever arm 50 to rise, thus rotating a lanyard 56 at a distal end of the lever arm 50 to apply tension to the pull-wire 22. FIGS. 4E and 4F show a pull-wire 22 threaded over a sliding pin 60 and a first fixed pin 62 and anchored to a second fixed pin 64. Advancing a control button 66 attached to the sliding pin 60 increases the tension in the pull-wire 22.

Figure 4G:
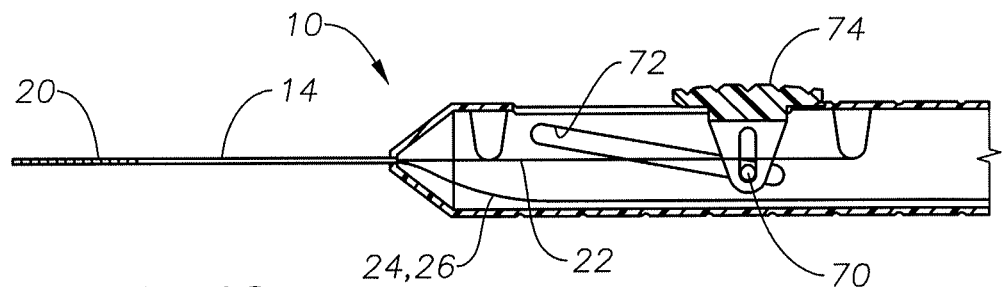
Figure 4H:
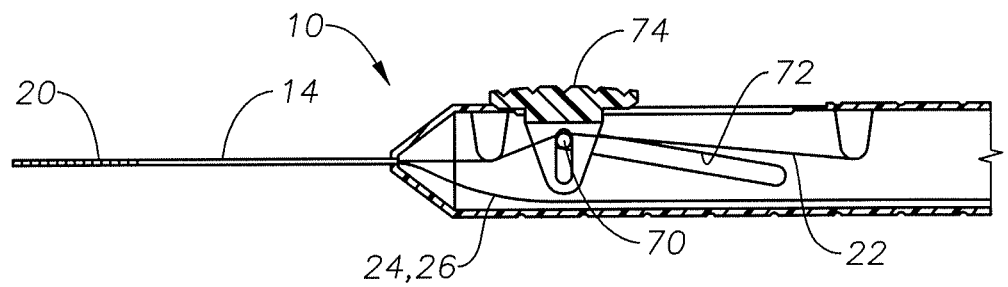
Figure 4I:
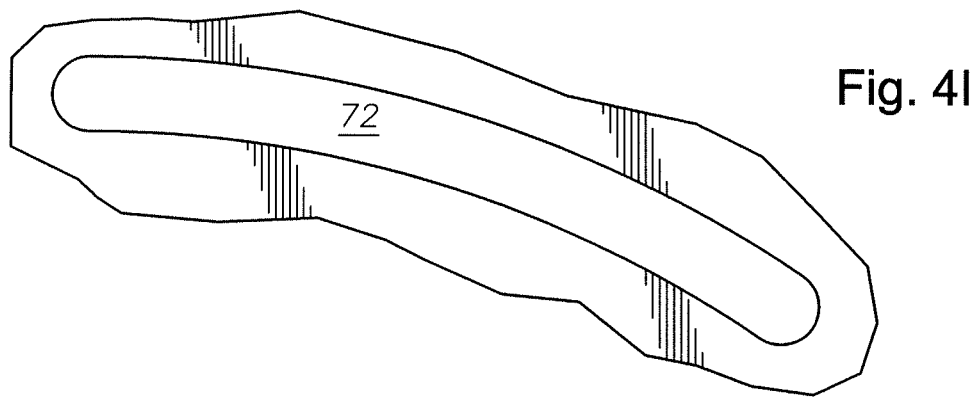
Figure 4J:
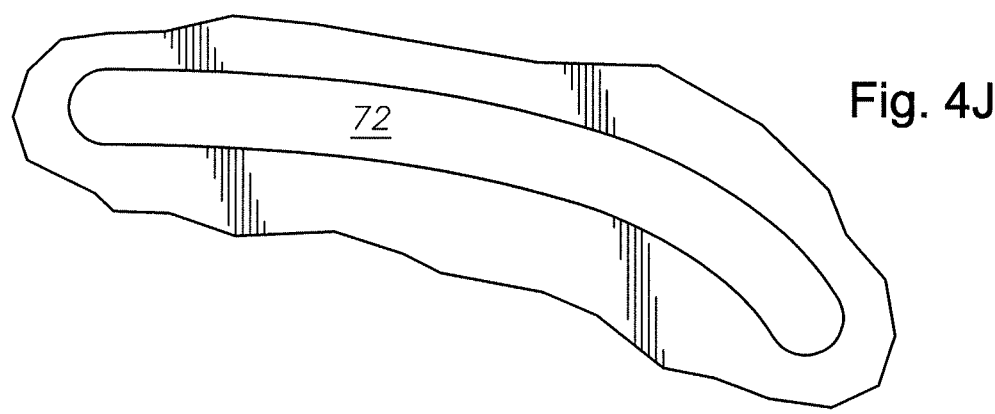
Figure 4K:
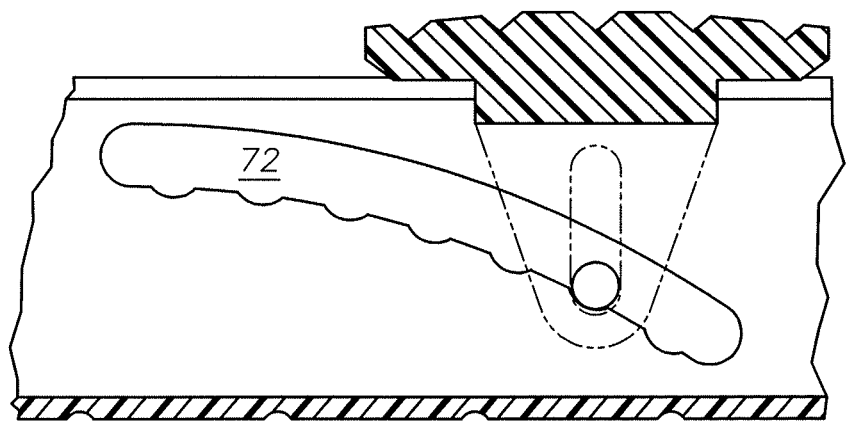

FIGS. 4G and 4H illustrate a pull-wire 22 threaded over a sliding pin 70 that is directed in a generally upward direction by a guide track 72 as a control button 74 is advanced. The path of the guide track 72 determines how the tension in the pull-wire 22 varies as the control button is advanced, thus providing a smooth and controlled increase in tension. In the case of a linear guide, like the one illustrated in FIGS. 4G and 4H, the pull-wire take up will occur in the latter portion of the advancement of the control button 74. In the alternative configuration shown in FIG. 4I, the guide track 72 is reshaped to provide greater take-up of the pull-wire at the beginning of the advancement by the control button 74 to produce a more balanced increase in tension throughout the stroke of the control button 74. In FIG. 4J, the guide track 72 inclines even more sharply so that most of the tension increase takes place early in the stroke of the control button 74. FIG. 4K illustrates an alternative embodiment of the guide track 72 with detents 80, allowing for distinct "stops" along the path corresponding to different angles of the slotted tip 20. A shelf or surface with detents can be also be used with any of the various embodiments of endoprobe 10 using a sliding pin or similar actuation mechanism, including any of the embodiments shown in FIGS. 4A-4K.

While certain embodiments of the present invention have been described above, these descriptions are given for purposes of illustration and explanation. Variations, changes, modifications and departures from the systems and methods disclosed above that would be apparent to one skilled in the art may be adopted without departure from the scope of the present invention as recited in the following claims.

What is claimed is:

1. An articulating optical surgical probe, comprising:
   a handle sized to fit in a single hand;
   a single rigid cannula extending from the handle having a diameter of 20 Ga or less, the single rigid cannula having a rigidity sufficient to substantially prevent bending relative to the longitudinal axis of the cannula during ordinary surgical use;
   a slotted tip comprising a plurality of slots spaced evenly along the entire length of said slotted tip, the slotted tip extending from a distal-most end of the single rigid cannula to a distal-most end of the articulating optical surgical probe;
   at least one optical fiber extending through the handle, the single rigid cannula, and the slotted tip to a distal end of the slotted tip; and
   a pull-wire extending through the slotted tip to a distal end of the slotted tip and a distal end of the at least one optical fiber:
   wherein the pull-wire is immovably secured to a second fixed object in the handle and suspended between a first fixed object in the handle and the second fixed object in the handle, the second fixed object located proximal to the first fixed object,
   wherein the pull-wire is suspended relative to and in non-contact with a sliding pin when the sliding pin is in a first position, the sliding pin being located between the first fixed object and the second fixed object,
   wherein, when the sliding pin is in the first position, the pull-wire is in a substantially straight orientation between the second fixed object and the distal end of the slotted tip and a tension on the pull-wire causes the slotted tip to rest in a straight position,
   wherein a distal movement of the sliding pin to an additional position contacting the pull-wire causes a deflection of the suspended pull-wire and an associated increase in the tension in the pull-wire, the increased tension causing the slotted tip to deviate from a straight position to a bent position, and
   wherein the slotted tip is formed from a resilient material that will restore to the straight position when the increased tension exerted by the pull-wire is released.

2. The probe of claim 1, further comprising a control button on the handle coupled to the sliding pin, wherein the distal movement of the sliding pin is controlled by sliding the control button.

3. The probe of claim 1, wherein the pull-wire is attached to a pinion, and the tension in the pull-wire is increased by winding the pull-wire around the pinion.

4. The probe of claim 1, further comprising a lever arm within the handle in contact with the pull-wire, the lever arm having a lowered position and a raised position, wherein the tension on the pull-wire is increased in the raised position.

5. The probe of claim 1, further comprising a plurality of detents in contact with the sliding pin, the detents providing a plurality of stops for advancement of the sliding pin.

6. The probe of claim 1, further comprising a guide track for the sliding pin within the handle, the guide track directing advancement of the sliding pin.

7. The probe of claim 6, wherein the guide track is linear.

8. The probe of claim 6, wherein the guide track is curved to control a rate of take-up for the pull-wire by the sliding pin so that the tension in the pull-wire increases uniformly as the sliding pin is advanced along the guide track.

9. The probe of claim 6, wherein the guide track is curved with an initial ramp at a proximal end such that a rate of increase in the tension in the pull wire is highest when the sliding pin is advanced through the initial ramp of the guide track, and the rate of increase in the tension declines after the sliding pin passes the initial ramp of the guide track.

10. The probe of claim 1, wherein the pull-wire is an optical fiber.

11. The probe of claim 1, wherein the slotted tip comprises deep slots extending past a radius of the slotted tip on a side toward which the slotted tip deviates and shallow slots extending short of the radius of the slotted tip on an opposite side from which the slotted tip deviates.

12. The probe of claim 11, wherein the deep slots are wider as a depth of the deep slots increases.

13. The probe of claim 11, wherein the deep slots comprise an oblong section extending longitudinally along the slotted tip.

14. The probe of claim 11, wherein the deep slots are curved.

15. The probe of claim 1, wherein the slotted tip comprises spiral slots.

16. The probe of claim 15, wherein the spiral slots have a spiral path perpendicular to a longitudinal axis of the slotted tip on a side to which the slotted tip deviates.

17. The probe of claim 15, wherein the slotted tip further comprises back slots interspersed between the spiral slots on a side to which the slotted tip deviates.

18. The probe of claim 15, wherein the spiral slots are wider on a side to which the slotted tip deviates.

19. The probe of claim 15, wherein the slotted tip is formed as a coil of wound wire.

20. The probe of claim 1, wherein the slotted tip is formed from nitinol.

21. The probe of claim 1, wherein the single rigid cannula is formed of stainless steel.

22. The probe of claim 1, wherein the single rigid cannula is coated with a stiffening material.

23. The probe of claim 1, wherein the slotted tip is coated with a soft polymer sheath.

24. The probe of claim 1, wherein the at least one optical fiber includes two optical fibers.

* * * * *